(12) United States Patent
Chibret et al.

(10) Patent No.: US 8,894,622 B2
(45) Date of Patent: Nov. 25, 2014

(54) BOTTLE FOR PACKAGING LIQUID THAT IS TO BE DISPENSED DROP BY DROP, WITH ANTIBACTERIAL PROTECTION

(75) Inventors: Jean-Frédéric Chibret, Clermont Ferrand (FR); Alain Defemme, Chamalieres (FR); Michel Faurie, Veyre-Monton (FR); Fabrice Mercier, Clermont Ferrand (FR)

(73) Assignee: Laboratoires Thea, Clermont Ferrand (FR)

( * ) Notice: Subject to any disclaimer, the term of this patent is extended or adjusted under 35 U.S.C. 154(b) by 224 days.

(21) Appl. No.: 13/055,725

(22) PCT Filed: Jul. 31, 2009

(86) PCT No.: PCT/IB2009/006420
§ 371 (c)(1),
(2), (4) Date: Jan. 25, 2011

(87) PCT Pub. No.: WO2010/013131
PCT Pub. Date: Feb. 4, 2010

(65) Prior Publication Data
US 2011/0125111 A1    May 26, 2011

(30) Foreign Application Priority Data
Jul. 31, 2008  (FR) ..................................... 08 04420

(51) Int. Cl.
*B65D 47/18*  (2006.01)
*A61F 9/00*   (2006.01)

(52) U.S. Cl.
CPC .............. *B65D 47/18* (2013.01); *A61F 9/0008* (2013.01)
USPC ........... 604/295; 604/294; 604/300; 222/420; 222/421; 222/422

(58) Field of Classification Search
USPC .......................... 604/294–295, 300, 289, 298; 222/212–215, 421, 476, 487, 490, 494, 222/570; 137/512, 846
See application file for complete search history.

(56) References Cited

U.S. PATENT DOCUMENTS 5,310,094 A * 5/1994 Martinez et al. .............. 222/212
5,373,972 A    12/1994 Bystrom et al.
(Continued)

FOREIGN PATENT DOCUMENTS

| WO | 0238464 A1 | 5/2002 |
| WO | 2006043295 A1 | 4/2006 |
| WO | 2007033480 A1 | 3/2007 |

OTHER PUBLICATIONS

World IP Organization. "International Search Report." PCT/IB2009/006420, Applicant: Laboratories Thea, Mailed: Jan. 12, 2010.

*Primary Examiner* — Loan H Thanh
*Assistant Examiner* — Andrew S Lo
(74) *Attorney, Agent, or Firm* — Millen, White, Zelano, Branigan, P.C.

(57) ABSTRACT

The present invention relates to a bottle for packaging a liquid to be distributed drop by drop comprising a reservoir the walls of which can be reversibly elastically deformed by letting air into the container, surmounted by a liquid dispensing head comprising a dropper nozzle protruding from the bottle and an anti-bacterial filter membrane, that is partially hydrophilic and partially hydrophobic, interposed across the path of the liquid and the air, at the base of the said nozzle. In the dispensing head, the proposal is to create the nozzle by itself out of a material containing a bactericidal agent that has the effect of preventing any bacterial growth on the surface of the said nozzle on the outside of the antibacterial membrane. A porous core is advantageously positioned inside the duct through which liquid is expelled and air is admitted.

9 Claims, 2 Drawing Sheets

(56) References Cited

U.S. PATENT DOCUMENTS

| | | | |
|---|---|---|---|
| 5,611,464 A * | 3/1997 | Tsao et al. | 222/189.06 |
| 2002/0187176 A1 * | 12/2002 | Yao | 424/405 |
| 2004/0074925 A1 * | 4/2004 | Faurie | 222/212 |
| 2007/0093765 A1 * | 4/2007 | Kawashiro et al. | 604/295 |
| 2007/0231295 A1 * | 10/2007 | Hoppe et al. | 424/78.09 |
| 2008/0177217 A1 * | 7/2008 | Polaschegg | 604/6.16 |

* cited by examiner

BOTTLE FOR PACKAGING LIQUID THAT IS TO BE DISPENSED DROP BY DROP, WITH ANTIBACTERIAL PROTECTION

The present invention relates to the design and production of a container bottle for a liquid to be dispensed drop by drop through a dispensing head with a dropper tip.

The invention applies to all fields in which it may be desirable to dispense a liquid drop by drop, notably for pharmaceutical products or cosmetic products or for any solution containing no antimicrobial preservative agents.

The particularly preferred field of application of the invention, which will be more specifically described in the present description as an example, without being in any way limiting, relates to the packaging and dispensing of ophthalmic liquids, which are intended to be applied locally in the eye, in the form of drops.

Most ophthalmic solutions, irrespective of their function (treatment of an eye disease, healing, hydration, etc.) are marketed contained in a reservoir inside a receiving bottle which is fitted with a dropper tip for its dispensing directly into the eye. The dropper is pierced with a central channel for the expulsion of the liquid from the inside reservoir to the outside. It is usually attached onto the reservoir. More precisely, in the bottles to which the present invention relates, the dropper forms part of a dispensing head in which it extends from an internal portion, or nacelle, which is sealingly inserted in the bottle neck and provides communication between the reservoir and the expulsion channel.

All the bottles of this type face a problem of protection against microbial proliferation with the risk, at the time of dispensing drops, of causing the microbiological contamination of the patient eye. As a remedy it is conventional practice to use antimicrobial preservative agents which are admixed into the solution. But such agents, such as for example benzalkonium chloride, have the serious drawback of being aggressive for the eye.

For the same purpose, it is an increasingly frequent practice to fit the drop delivering systems with an antibacterial filtering membrane interposed across the liquid path between the reservoir and the dropper tip in order to prevent external contaminants reaching the solution contained in the reservoir. This solution is satisfactory with respect to the content of the bottle and so long as the bottle remains protected by a cap enclosing the dropper tip and by the overall packing. It is no longer so after the dispensing head has been uncovered for a first use, which makes it necessary to limit the duration of the bottles currently in use in order to prevent the occurrence of unwanted eye infections.

Some people have also considered they could solve the problem by adopting arrangements which exist in other sectors, where water-flow circuits are produced which consist of a material having a bactericidal activity. This is the case with patent document WO 2007/056131 which avoids the use of, an antibacterial filtering membrane by making provision to treat in this way a non-return valve through which the liquid is expelled from a bottle. In addition to the fact that this solution has not proven to have the desired effectiveness, it is reserved for bottles with irreversible deformation in which the volume of the liquid reservoir reduces with each use and no intake of air replaces the liquid consumed.

The object of the present invention is essentially to improve the health conditions associated with the use of a bottle for packaging liquid in which the liquid reservoir has a wall with reversible elastic deformation by letting air into the reservoir to replace any volume of liquid expelled and in which the air is let in through the dispensing head via the same route as the expulsion of liquid. A further object is to take full advantage of the possibilities offered by the antibacterial membranes by proposing a bottle suitable for the packaging of ophthalmic solutions with no preservative.

As the origin of the invention, it was observed that with this type of bottle, the risk of eye contamination does not come so much from the instilled liquid as from the bottle-making itself, wherein the tip is exposed to being touched by the user, to being left without its cap between two uses and to being brought too close to the eyelids.

In the bottle proposed by the invention, the head for dispensing liquid drop by drop comprises an antibacterial filtering membrane which is interposed in the path of the expelled liquid and of the air entering in compensation and which is mounted between a nacelle for sealed mounting on the bottle in communication with its internal reservoir and the dropper tip, and it is proposed to produce the dropper only, to the exclusion of the nacelle, from a material containing a bactericidal agent having an effect in antibacterial prevention of a bacterial proliferation on its external surface.

Bottles comprising such an antibacterial filtering membrane are already known per se; they prevent the bacteria that could be borne by the air entering the bottle after the expulsion of a drop of liquid from reaching the reservoir to contaminate the remaining liquid. This membrane comprises no bactericidal agent; its antibacterial action comes from its filtering properties: it prevents the bacteria from passing through it, the mean diameter of a pore of the membrane being less than or equal to 0.2 µm (for example from 0.1 to 0.2 µm). The presence of this membrane makes it possible to use the bottle for packaging a liquid which does not need to contain a preservative agent, provided however that the product is used only for a limited time after the bottle is opened. In general, one month of use at most is recommended.

Yet more specifically, the subject of the invention is a bottle for packaging a liquid which comprises a reservoir with a wall with elastic deformation that is reversible by letting air into the receptacle in order to deliver the liquid under the effect of a pressure exerted against this wall and in order to allow a spontaneous return of the receptacle to its initial conformation after delivery of a dose of liquid, the antibacterial filtering membrane being partially hydrophilic and partially hydrophobic. The operating principle of such a bottle has been described in detail in international patent application WO 2006/000897.

In the case of such bottles, use is made of a bifunctional membrane, which is partially hydrophilic and partially hydrophobic, for example made of polyamide-based or polyethersulfone-based polymer, which allows, on the one hand, liquid to pass through in the dispensing direction, under the effect of a pressure exerted by the user on the wall of the reservoir, and, on the other hand, air to pass in the reverse direction, from the outside to the reservoir, when this pressure is released after the dispensing of a drop of liquid. It is possible to buy a filtering membrane commercially, which is made partially hydrophobic on one portion of its surface, by modifying its structure notably by grafting in the presence of a radical-reaction initiator, so as to allow air to pass through from the outside to the reservoir after each dispensing operation. This treatment is notably carried out on a median strip occupying 20 to 50% of its surface area placed across the path of the liquid.

Moreover, a bottle as described in international patent application WO 2006/000897 comprises a hydrophobic microporous pad regulating the flow of liquid to be delivered, situated between the liquid-storage reservoir and the filtering membrane. It also comprises a cap for protecting the tip creating a seal when the bottle is not used for delivering liquid.

According to the invention, only the dropper tip, which is, situated beyond this antibacterial filtering membrane, is treated with a bactericidal agent. Accordingly, the liquid remaining in the reservoir does not come into contact with the surfaces of the portions in which the material contains a bactericidal agent. This therefore prevents the bactericidal agents from spoiling the liquid remaining in the reservoir over time. Supposing even that tiny fractions of liquid can enter the bottle after drop by drop expulsion of the liquid, this liquid, just like the pressure-balancing aspirated air will have been filtered of any bacterium on passing through the membrane before entering the reservoir.

In patent application WO 2007/056131, a bottle has been proposed for packaging a liquid to be dispensed drop by drop with an tip forming a valve through which the liquid is expelled without letting the slightest amount of air into the reservoir containing the liquid. When, in this document, it is also recommended that the materials constituting this tip or the whole bottle assembly be treated by a bactericidal agent, this can involve only treating the liquid as it passes through.

According to a preferred embodiment of the invention, the body of the dropper tip is formed of a material, notably of a molded polymer material, which contains a polymer bearing ions with a bactericidal effect uniformly distributed in its mass.

The ion-bearing polymer chosen in the context of the invention advantageously has, by virtue of the bactericidal properties of the ions that it bears, an effective antimicrobial action against bacterial strains but also against yeasts and molds. The ions in question are in particular silver ions. It has been found by the inventors that bottles fitted with such a dropper tip advantageously provide good biological safety for the patient while having no toxicity for the eye.

The antibacterial effect is advantageously exerted on the surface of the dropper tip. The bactericidal ions that are present on this surface, and notably on the surface which risks coming into contact with the eye, exert in this location a bacteriostatic effect inhibiting the bacterial proliferation which can begin after the contamination of the tip. This bacterial contamination may for example come from bacteria present in the eye or around the latter, by contact of the tip with the occular tissues or fluids when the drops are administered. This contamination can also emanate, more generally, from intentional or unintentional contact with the fingers of the user at the time of dispensing, or quite simply from the ambient air or from a foreign body when the tip is not protected by a cap between two uses. Moreover, liquid residues, of the order of a few microliters, are always reaspirated into the tip after each dispensing operation if only in the expulsion channel. These residues constitute a favorable moist medium capable of forming a source for a microbial proliferation in the tip.

Over time and various uses, it is possible to think that the bactericidal, ions present in the material migrate into the polymer bearing them, in the direction of the surface of the tip, so as to replace the ions consumed progressively as they act from this surface.

The dropper tip according to the invention therefore advantageously remains always protected on both its external and internal surfaces, from the microbial proliferation that might engender bacterial concentrations that are sufficiently large to be harmful to the health or the comfort of the user. In particular, this prevents the liquid that passes through the tip at the time of dispensing from being contaminated. The tip also never forms a source of direct contamination of the eye, by contact of the tip with the eye at the time of a subsequent dispensing. In the case of the dispensing tips incorporating at their base an antibacterial membrane to prevent contamination of the liquid inside the reservoir, this also reduces the risk of a biological film or biofilm forming on the surface of the dropper tip, which would systematically contaminate the liquid when it passes through the membrane during dispensing.

The method for manufacturing the tip according to the invention is advantageously quite simple to implement. The particles of polymer charged with ions having a bactericidal effect are inserted into the polymer material so as to obtain, after heating, a uniform mixture from which the process of molding the tip is carried out.

This method, compared with the conventional methods for manufacturing dispensing tips by molding, requires only one simple additional step, that is to say the mixing of the antibacterial polymer with the main material forming the tip to be molded at the very beginning of the molding process.

The silver ions are most particularly preferred as ions with a bactericidal effect. These ions are known conventionally, for their antimicrobial properties while they have no toxicity for the human eye in the concentration of a few percent of silver ion-bearing polymer in the mass. They are effective against most bacteria, yeasts, funguses and other similar microbes. They bind to the membrane of the cells and disrupt its natural function. They also penetrate through the walls of the cells in which they combine with electron donor groups and negatively charged groups, and with thiol groups common in the enzymes. This causes a malfunction of the cells which rapidly leads to their death.

The silver ions are for example inserted into the material in the form of granules containing them as a fine dispersion in polyethylene, carried by an inorganic ion-exchange resin. Such granules are commercially available and they notably have the advantage of being extremely easy and safe to use.

The proportion of bactericidal ion-bearing polymer particles that are incorporated into the mixture in order to form the body of the tip is advantageously between 1 and 10% and preferably between 2 and 5% by weight of the total weight of the mixture.

The dropper tip according to the invention can be formed as a single annular piece, pierced with a narrow central channel for the expulsion of the liquid.

According to a particularly advantageous embodiment of the invention, the dropper tip is made so as to divide the flow cross-area available as a path for the expelled liquid or the reaspirated air into several circuits limited by surfaces of a material loaded with bactericidal doping agent. Accordingly, the invention makes provision notably to arrange in the tip a relatively wide inner central channel in which a central core is inserted, forming a plurality of subchannels for the expulsion of the liquid, and to produce this central core in a material containing a bactericidal agent distributed in its mass.

One advantage of this central core is that the effectiveness in terms of inhibiting the bacterial proliferation of the tip is further enhanced, since the contact surface offered to the air entering from the outside, and therefore to the source of external bacterial contamination, by the subchannel walls made of antimicrobial material, is greater than in the case of a single channel.

According to one advantageous feature of the invention, the central core comprises a different bactericidal agent than that contained in the external body of the tip (the external portion). This makes it possible to extend the effectiveness against bacterial proliferation; it is possible specifically to combine bactericidal agents having antibacterial spectra that are different and best suited depending on the portions of the tip. As explained above, the bactericidal agents bearing ions such as silver ions release these bactericidal ions over time and have a worthwhile action for the external surfaces of the tip and for countering the formation of biofilms.

According to a particular, feature of the invention, the central core comprises as a bactericidal agent a compound chosen from phenolic compounds and notably chlorinated phenolic compounds. Preferably this chlorinated phenolic compound is 5-chloro-2-(2,4-dichlorophenoxy)phenol, known under the commercial name of triclosan. This compound has a broad antibacterial spectrum. According to certain studies, this compound has a biocidal action through action on the membrane and/or the cytoplasm of bacteria and a bacteriostatic action preventing the proliferation of bacteria by inhibiting mainly the synthesis of fatty acids necessary to the reproduction and construction of cellular membranes.

According to an advantageous feature of the invention, the central core is formed of the same base material as that used to form the main external body of the dropper tip.

The central core and the main external, body of the tip, which delimits the central channel, are each manufactured independently from one another in distinct molding operations, then assembled to one another by inserting the core into the channel.

In such an embodiment, the invention advantageously makes provision for the subchannels to be formed by grooves hollowed out of the external surface of the core. This feature is particularly advantageous because it allows better control of the surface state of the walls of the expulsion channel, in consideration of the method for manufacturing the tip.

Specifically, in the case of conventional droppers, that comprise a narrow central channel for the expulsion of the liquid, the formation of the channel is carried out after the molding process, by piercing through the material by means of a very fine needle while said material is still not completely cured. In industrial production, such a method can create microirregularities on the surface of the central channel and cause the formation of retention micro-pockets on the wall thickness of the channel, which micro-pockets constitute niches for the proliferation of bacteria.

In a preferred dropper tip according to the invention, the channel for expelling the liquid comprises a plurality of subchannels. These subchannels, through their manufacturing method, by which the grooves are formed during the molding of the core by means of a mold of appropriate shape, have smoother walls which have no surface asperities in which bacteria and other microbes can lodge and proliferate.

The subchannels are preferably at least two in number, preferably four, and evenly distributed about the axis of the core, so as to provide a considerable area of contact with the air aspirated into the tip after each dispensing operation.

According to another preferred embodiment of the invention, the central core is made of a porous thermoplastic material, in particular a material based on polyolefins, and more particularly chosen from the families of polyethylenes (such as can also be the main external, body of the tip). Polyethylenes confer on this material a hydrophobic quality which prevents liquid stagnation.

Such a porous material is preferably a sintered material. It is then obtained by sintering, that is to say by heat treatment of particles of the thermoplastic polymer, previously coldcompressed in a mold, said heating being carried out at a temperature below that of the melting point of the polymer (the main component). This manufacturing method makes it possible to bind the particles together without melting them and to control the porosity of the material, especially by acting on the conditions of temperature and pressure. The bactericidal agent can be added in various ways, i.e. in the mass together with the base polymer, or by mixing a bactericidal-treated polymer and the base polymer, or else by surface treatment with or without additives. Specifically, the porous polymer material can be made by sintering and then the sintered material obtained is treated by the bactericidal agent. Such porous materials and their manufacturing methods are described for example in international patent application WO 01/65937.

Advantageously, in this embodiment of the invention, the porous thermoplastic material has a mean pore dimension, the order of magnitude of which is some hundred micrometers. This dimension may for example range between 0.1 and 0.2 mm (100 and 200 µm).

Also advantageously in this embodiment of the invention, the porous material and the terminal portion of the external part of the dropper tip have similar cylindrical shapes that match, that is to say that closely conform to one another. This makes it possible to prevent the liquid stagnating between the wall of this portion of the tip and the central core. This cylindrical shape of the central core is a compromise which minimizes the pressure loss when the liquid passes through it in order to be dispensed and moreover optimizes the antibacterial contact surfaces. According to a particular case of this embodiment, the terminal portion of the tip has an overmolded shape on the porous material. It is produced by overmolding on the porous material so that shapes match exactly.

In preferred embodiments of the invention, the dropper tip comprises, at the base of the central channel, a peripheral boss which interacts with a matching peripheral groove formed at the base of the core for the attachment of the core into the channel by elastic snap-fitting effect. The core is forced into the channel and it is firmly held inside the latter by the boss formed at its base. The boss and the groove are formed during molding the tip, respectively that of its external portion, which delimitates the central channel, and that of its core.

The invention will now be more completely described in the context of preferred features and of their advantages with reference to FIGS. 1 to 5 in which.

Figure 1:
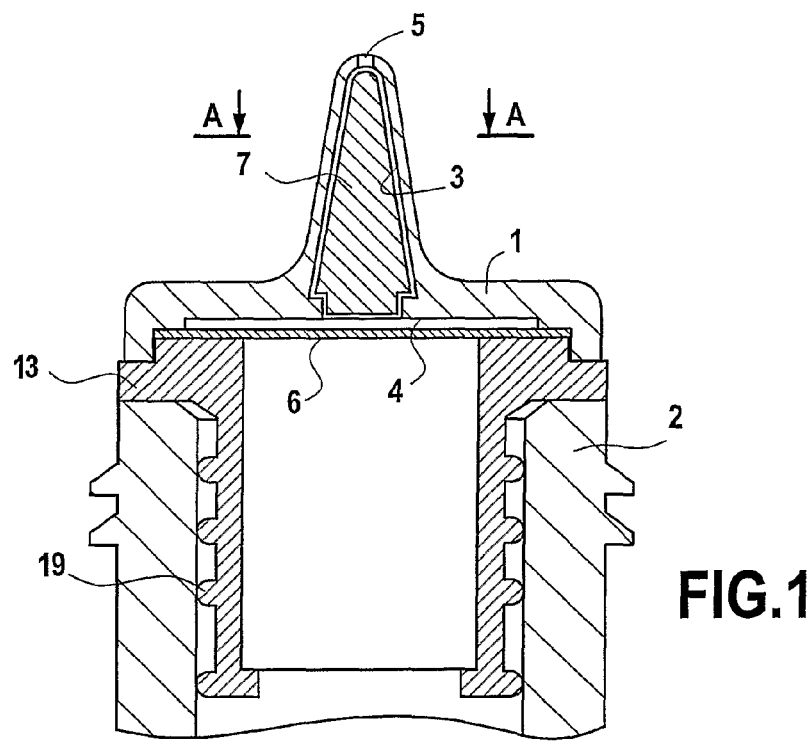
FIG. 1 represents a cross-sectional view along a longitudinal plane showing the dropper tip of a dispensing head according to the invention.

An example of a first type of a dropper tip 1 of a dispensing head according to the invention is shown in FIG. 1.

The dispensing head comprises a nacelle 13 which is designed to be mounted in a sealed manner, by virtue of sealing flutes 19, inside the neck of the bottle 2. The tip 1 extends it along its axis. It is welded thereto at its base 4.

The bottle comprises a reservoir, not shown in the figure, which is enclosed by a wall with reversible elastic deformation which is designed to contain an eye-drop fluid and advantageously a preservative-free eye-drop solution. When the flexible wall of the reservoir is pressed manually, the liquid is forced through a flow-regulating pad placed in the internal duct of the nacelle 13. The spontaneous return of the reservoir to its original shape causes an intake of air through the same duct.

The dropper tip comprises a longitudinal central channel 3, which passes through the whole of its height from the base 4 of the tip to the liquid-expulsion orifice 5, situated at its top end (considering the bottle placed vertical).

Under the base of the tip 1, an antibacterial filtering membrane 6 is placed across the passage of the liquid from the reservoir to the tip and of the incoming air. This membrane is designed to protect the liquid contained in the reservoir from external contamination.

The body 12 of the tip is made of a polymer material, notably of a polymer of the polyethylene type, incorporating in the mass a polymer bearing ions with a bactericidal effect. This polymer is chosen to be compatible with the conventional material of the tip. If only for this reason, it is preferably polyethylene-based. It is available commercially in the form of powder or of granules or of beads, ready to be incorporated into the molding compound of the tip. The bactericidal agent preferably consists of silver ions which are borne by the polymer macromolecules.

Such silver ions are known to be effective on many bacterial strains, yeasts and molds, notably on the *Pseudomonas* and *Staphylococcus* strains, most widely present on the skin and the occular mucosa. With respect to commercial products made of polymer, particularly of polyethylene, charged with silver ions, that can be used in the context of the invention; it is possible for example to cite AlphaSan® from Clariant S.p.A. or Biomaster sold by Addmaster Ltd.

The tip according to the invention is manufactured according to a conventional molding process based on the mixture containing the antimicrobial polymer as a uniform mixture with the polyethylene. The proportion of polymer granules bearing silver in the polyethylene is approximately 5% by weight.

After the molding process, the bactericidal agent is present throughout the mass of the tip, and in particular both on the outer surface that can come in contact with the user's eyes or hands and on its inner surface that delimitates the axial expulsion channel 3.

Figure 2:
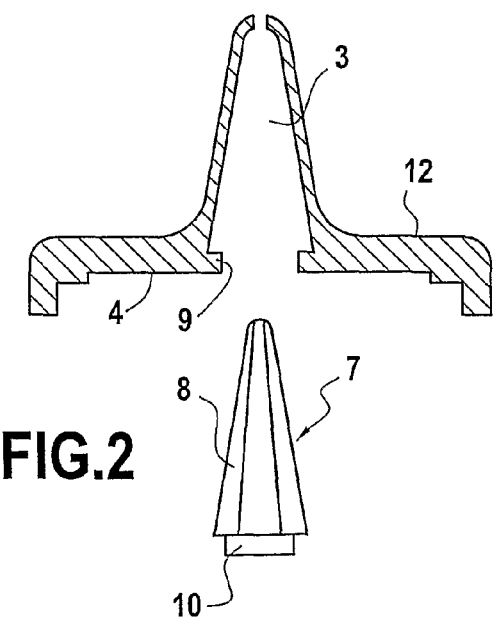
FIG. 2 illustrates, in perspective view, the central core of the tip of FIG. 1, and in cross-sectional view along a longitudinal plane, its receiving housing in the tip.

Inside the central channel 3 of the tip, an inner core 7 is placed as shown in perspective view on FIG. 2. The core 7 has a shape that matches that of the central channel 3 in which it is housed, that is to say a generally conical shape widening out from top to bottom. Its external diameter is adjusted to the internal diameter of the channel 3 so that the liquid cannot travel between the channel and the core.

On the external surface of the core 7, four grooves 8 are formed evenly distributed about the axis of the core 7.

The central core 7 is manufactured via a molding process from the same base material, notably polyethylene, as the body 12 of the tip which surrounds it, but advantageously it comprises a bactericidal agent that differs from that contained in the body 12 in order to have effect on the external surface of the tip. This bactericidal agent is triclosan in this instance. Triclosan has a broad antibacterial (and also antifungal) spectrum. The grooves 8 on its surface are formed during the molding process by a specifically adapted form of the mold.

Figure 3:
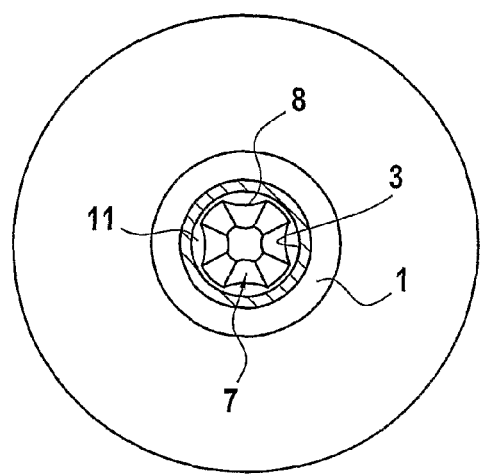
FIG. 3 shows a cross-sectional view along the plane A-A of the tip of FIG. 1.

When the core 7 is placed in the channel 3, as illustrated in FIG. 3, subchannels 11 of small cross section are formed between the external wall of the core 7 and the internal wall of the channel 3 at the level of the grooves 8. These subchannels 11 provide a passageway for the liquid from the base of the tip to the expulsion orifice 5. Their surface, of contact with the air is smooth and even, with no stagnation zone for the air, the liquid and the bacteria.

At the base of the central channel 3, the tip 1 comprises an annular boss 9 reducing the diameter of the channel at this location. The core 7, for its part, comprises also at its base an annular groove 10 matching the boss 9.

The external portion 12 of the tip 1 and the core 7 are each manufactured using a conventional molding process and then assembled to one another.

During the mounting of the tip according to the invention, the core 7 is inserted by a forceful engagement in the channel 3 until it butts against the top end of the tip surrounding the expulsion channel, which forms the ring for releasing the drop. In this position, the groove 10 is facing the boss 9. These two elements interact via an elastic snap-fitting effect in order to provide a solid hold of the core inside the channel.

According to its preferred embodiment, the invention makes provision to replace the above grooved core with a porous core inserted in the same manner in the expulsion channel passing through the tip in order to perform the same function of dividing the flow of liquid by distributing it in a plurality of circuits through the expulsion channel pierced in the tip.

There are many advantages thereof. On the one hand, the flow is much more divided and the distribution is finer. On the other hand, the channel can be better filled uniformly by the material swept by the liquid when it is expelled. Furthermore, it is in combination with the porous shape that the use of a bactericidal agent of the family of chlorinated phenolic organic compounds rather than an ionic agent is of most value for efficacy against the risks of occular contamination.

Figure 4:
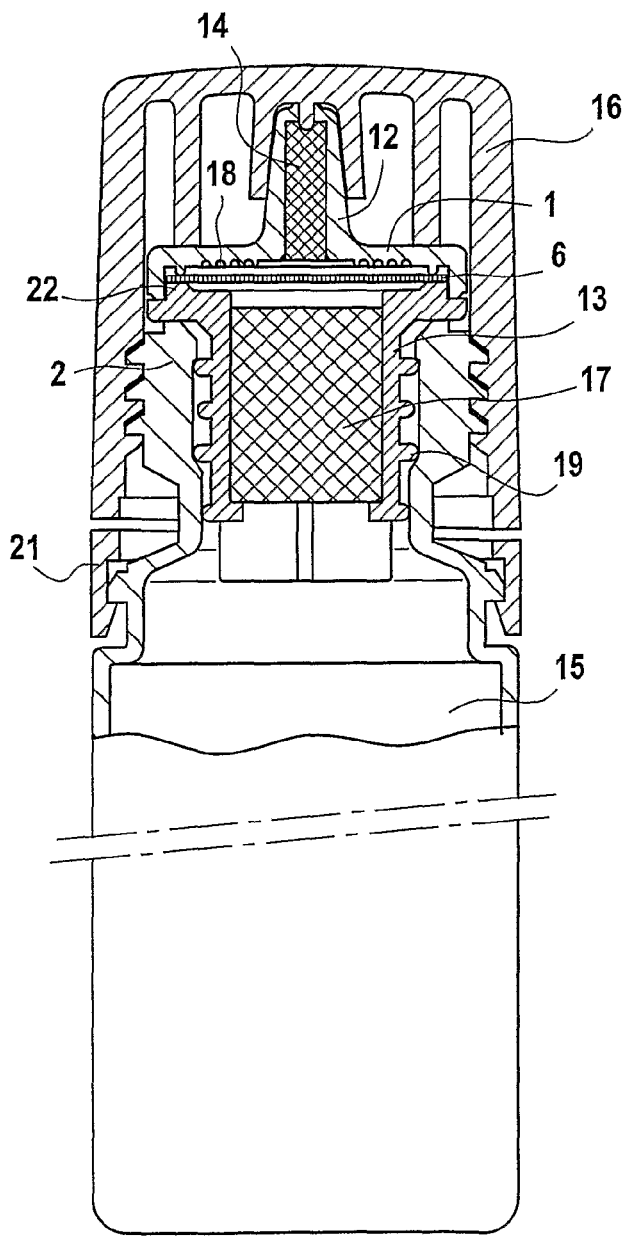
FIG. 4 represents a cross-sectional view along a longitudinal plane of an tip with the porous central core according to the invention.

A bottle fitted with such a dispensing head is shown in FIG. 4.

As above, the dispensing head comprises a nacelle 13 to which the tip 1 is secured in order to, form an insert that has been forced into the neck 2 of the bottle. At the other end from the tip, the nacelle terminates in the bottle with four radial cruciform walls.

The nacelle 13 of the dispensing head is mounted in a sealed manner by virtue, of the sealing flutes 19 inside the neck 2 of the bottle from which the tip 1 protrudes which extends in the axis of the bottle. The inside of the bottle holds a reservoir 15, limited by a cylindrical wall with reversible elastic deformation, which is designed to contain a collyrium, advantageously containing no preservative. A protective cap 16 and a tamper-proof ring 21 complete the assembly externally.

The neck 2 of the bottle comprises, under the base of the tip 1, an antibacterial filtering membrane 6 placed across the path of the liquid from the reservoir to the tip and of the incoming air. It is freely supported in operation by application against the base of the tip. It is attached on its periphery by heat sealing between a peripheral ring of this base (which here has a swelling 20 which flattens out during the sealing operation between the two parts) and an interacting bearing surface 22 on the terminal face of the nacelle.

A microporous pad 17 is placed in the central bore of the dispensing head. In itself it is conventional, including in its function in regulating the liquid flows and balancing air pressures. It structure is that of a felt of intermingled threads, at a density corresponding to an equivalent pore diameter of the order of 50 microns.

Circular recesses 18 make it possible to drain the flow of liquid forced through the filtering membrane 6 to the central expulsion channel 3.

The body 12 of the tip is made as described above for the other tip of FIG. 1 but its top portion is cylindrical (instead of being conical). This main body 12 is made of a polymer material, based on polyethylene, comprising a silver-ion-bearing polymer bactericidal agent.

Figure 5:
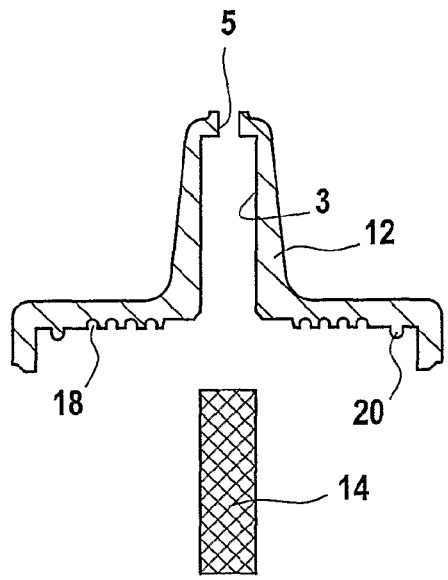
FIG. 5 depicts a porous cylindrical core (14), of a shape to match that of the top portion of the tip, and of a size to fill the central channel (3) of the tip.

The central core 14 which is shown in perspective view in FIG. 5, is a porous cylindrical core, of a shape to match that of the top portion of the tip, and of a size to fill the central channel 3 of the tip. This porous core occupies all the space of the central channel 3 in order to have the largest possible contact surface with the micro-drops of liquid or the air entering the tip after expulsion of a drop of liquid during its use. This also prevents pressure losses caused when it is passed through by the liquid going out.

This porous core has a length in the order of magnitude of a centimeter, namely notably a length of between 0.5 and 2.5 cm, and a diameter in the order of magnitude of a millimeter more particularly ranging between 2 and 6 millimeters.

This central core 14 is made of a porous thermoplastic material, based on sintered polyethylene, comprising a bactericidal agent consisting of an organic molecule diffused in the mass of the polymer, and not a polymer having metal ions as for the body of the tip. In this example, the core 14 made of sintered material comprises triclosan while the external portion 12 of the tip comprises a silver-ion-based bactericidal agent.

Its mean pore diameter is in the order of magnitude of a tenth of a millimeter, and more particularly of the order of 150 μm. Such a porous material is notably sold by POREX Corporation.

This central core 14 has been forced into the central channel 3 of the tip.

According to another embodiment, the external portion 12 of the tip is made by overmolding of the porous core 14. This overmolding makes it possible to have an tip of which the shapes respectively of the central core 14 and of the portion of the central channel 3 match perfectly. This makes it possible to prevent the liquid stagnating between the wall of this portion of the tip and the central core.

The dispensing heads of the bottles with the two types of tips presented as examples according to the invention thus constituted have a considerable antimicrobial effect both in the external wall of the tip, capable of being contaminated by the external environment, and in the walls of the liquid expulsion channels which are capable of being contaminated by the air and the liquid residues reaspirated from the outside after each liquid dispensing operation. This antimicrobial effect, which has been found effective against the usual contaminants in the occular environment, inhibits the bacterial proliferation on these surfaces and makes it possible to keep a hygienic tip ensuring the microbiological safety of the eye of the consumer.

The aforegoing description clearly explains how the invention makes it possible to achieve the objectives that it has set for itself. In particular, it provides a bottle for packaging liquid, notably ophthalmic liquid, with a dropper tip which maintains, by an antibacterial effect, a microbiologically hygienic state throughout the period of its use and which thereby provides good microbiological safety for the user.

It nevertheless arises from the aforegoing that the invention is not limited to the embodiments that have been specifically described and represented in the figures and that, by contrast, it extends to any variant making use of equivalent means.

The invention claimed is:

1. A bottle for dispensing a preservative-free liquid to be dispensed drop by drop comprising a dispensing head and a reservoir with a wall capable of elastic deformation, the deformation being reversible by letting air into said reservoir to replace any volume of liquid expelled by means of said dispensing head through which liquid is delivered under the effect of a pressure exerted against said wall, air being let in through the dispensing head via the same route as the expulsion of liquid, wherein said dispensing head which is fitted in a sealed manner into said bottle comprises a dropper tip which extends outside of said bottle and which is pierced with a central channel leading to an orifice for expulsion of liquid, said dropper tip comprising a body having a base, and a core which is inserted into said central channel, wherein a partially hydrophilic and partially hydrophobic antibacterial filtering membrane, is mounted on the base of said dropper tip, and is interposed across a passage for liquid and air, so as to allow liquid flowing in a dispensing direction from the reservoir to the dropper tip, under the effect of a pressure exerted by a user on said wall to pass through said filtering membrane, and to allow air flowing in a reverse direction from the dropper tip to the reservoir, when said pressure is released after the dispensing of a drop of liquid, to pass through said filtering membrane while preventing the passage of bacteria from outside of said bottle into said reservoir, whereby air passes into the dispensing head via the same route as liquid that is dispensed from said reservoir, wherein selectively said body and said core, which are situated beyond said partially hydrophilic and partially hydrophobic antibacterial filtering membrane in the dispensing direction, are both made of a material containing a bactericidal agent, and wherein said core comprises a plurality of subchannels for the expulsion of liquid and the intake of air in compensation, said subchannels being formed by grooves hollowed out on an external surface of said core.

2. The bottle as claimed in claim 1, wherein said core is made of a material comprising a bactericidal agent based on a chlorinated phenolic compound.

3. The bottle as claimed in claim 1, wherein said material forming said core contains 5 chloro-2-(2,4-dichlorophenoxy) phenol or triclosan as said bactericidal agent.

4. The bottle as claimed in claim 1, wherein said core has an axis and at least two of said subchannels, evenly distributed about the axis of said core.

5. The bottle as claimed in claim 1,
wherein said core inside the dropper tip is a porous sintered thermoplastic material based on polyethylene.

6. The bottle as claimed in claim 5, wherein said porous sintered thermoplastic material has a mean pore dimension, the order of magnitude of which is between 100 and 200 micrometers.

7. The bottle as claimed in claim 6, wherein said body is made by overmolding of the porous sintered thermoplastic material.

8. The bottle as claimed in claim 4, wherein said subchannels are four in number.

9. A bottle for dispensing a preservative-free liquid to be dispensed drop by drop comprising a dispensing head and a reservoir with a wall capable of elastic deformation, the deformation being reversible by letting air into said reservoir to replace any volume of liquid expelled by means of said dispensing head through which liquid is delivered under the effect of a pressure exerted against said wall, air being let in through the dispensing head via the same route as the expulsion of liquid, wherein said dispensing head which is fitted in a sealed manner into said bottle comprises a dropper tip having a base, wherein said dropper tip extends outside of said bottle and which is pierced with a central channel leading to an orifice for expulsion of liquid, wherein a partially hydrophilic and partially hydrophobic antibacterial filtering membrane, is mounted on the base of said dropper tip, and is interposed across a passage for liquid and air, so as to allow liquid flowing in a dispensing direction from the reservoir to the dropper tip, under the effect of a pressure exerted by a user on said wall to pass through said filtering membrane, and to allow air flowing in a reverse direction from the dropper tip to the reservoir, when said pressure is released after the dispensing of a drop of liquid, to pass through said filtering membrane while preventing the passage of bacteria from outside of said bottle into said reservoir, whereby air passes into the dispensing head via the same route as liquid that is dispensed from said reservoir, wherein selectively said dropper tip and a core, which are situated beyond said partially hydrophilic and partially hydrophobic antibacterial filtering membrane in the dispensing direction, are made of a material containing a bactericidal for preventing bacterial proliferation on a surface of said material, and wherein, at a base of said central channel, a peripheral boss interacts with a matching peripheral groove formed at a base of said core for the attachment by elastic snap-fitting effect of said core into said channel.

* * * * *